United States Patent [19]

Ko

[11] Patent Number: 4,690,149
[45] Date of Patent: Sep. 1, 1987

[54] NON-INVASIVE ELECTROMAGNETIC TECHNIQUE FOR MONITORING PHYSIOLOGICAL CHANGES IN THE BRAIN

[75] Inventor: Harvey W. Ko, Columbia, Md.

[73] Assignee: The Johns Hopkins University, Baltimore, Md.

[21] Appl. No.: 791,864

[22] Filed: Oct. 28, 1985

[51] Int. Cl.[4] ............................................. A61B 5/05
[52] U.S. Cl. .................................... 128/653; 128/734
[58] Field of Search ................................ 128/1.3–1.5, 128/653, 734, 748, 630

[56] References Cited

U.S. PATENT DOCUMENTS

| 3,789,834 | 2/1974 | Duroux | 128/1.3 |
| 4,066,065 | 1/1978 | Kraus | 128/1.5 |
| 4,270,545 | 6/1981 | Rodler | 128/653 |
| 4,281,667 | 8/1981 | Cusman | 128/748 |
| 4,561,426 | 12/1985 | Stewart | 128/1.5 |

FOREIGN PATENT DOCUMENTS

| 1113156 | 11/1981 | Canada | 128/1.5 |
| 618405 | 2/1949 | United Kingdom | 128/653 |
| 0764653 | 9/1980 | U.S.S.R. | 128/734 |

OTHER PUBLICATIONS

Robillard et al., "Specific Impedance Measurements of Brain Tissues", Med. & Biol. Eng. & Comput., Jul. 1977, vol. 15, pp. 438–445.

Primary Examiner—Kyle L. Howell
Assistant Examiner—Ruth S. Smith
Attorney, Agent, or Firm—Robert E. Archibald; Howard W. Califano

[57] ABSTRACT

An apparatus and method for non-invasively sensing physiological changes in the brain is disclosed. The apparatus and method uses an electromagnetic field to measure localized impedance changes in brain matter and fluid. Various spatial and temporal techniques are used to localize impedance changes in the brain. The apparatus and method has particular application in locating and providing time-trend measurements of the process of brain edema or the process of hydrocephalus.

7 Claims, 14 Drawing Figures

|  |  | TEMPERATURE (°C) | | | |
| --- | --- | --- | --- | --- | --- |
|  |  | 12 | 13 | 20 | |
| WHITE | NORMAL | 0.15 ± 0.03 | 0.15 ± 0.01 | 0.14 ± 0.02 | CONDUCTIVITY IN mho/METER |
|  | EDEMATOUS | 0.16 ± 0.01 | 0.18 ± 0.01 | 0.18 ± 0.01 | |
| GREY | NORMAL | 0.20 ± 0.01 | 0.21 ± 0.02 | 0.12 ± 0.02 | |
|  | EDEMATOUS | 0.38 ± 0.04 | 0.30 ± 0.07 | 0.36 ± 0.07 | |
FIG. 1
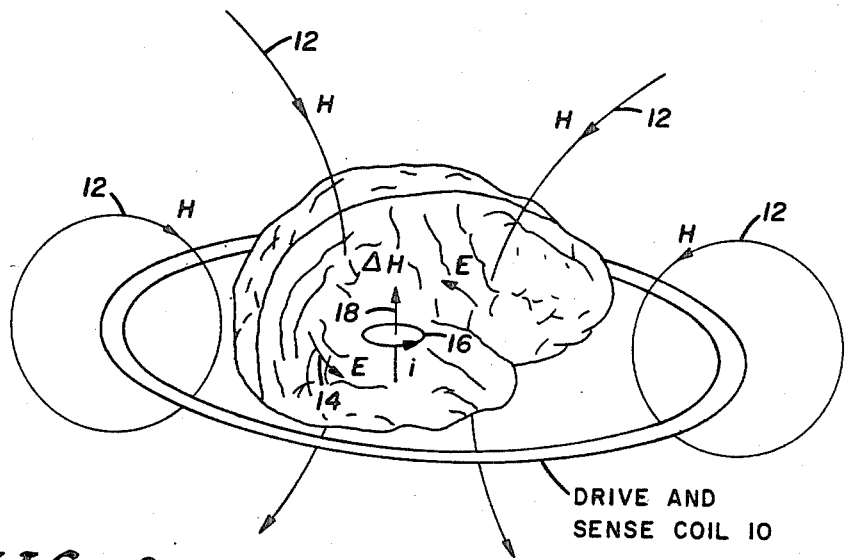
FIG. 2
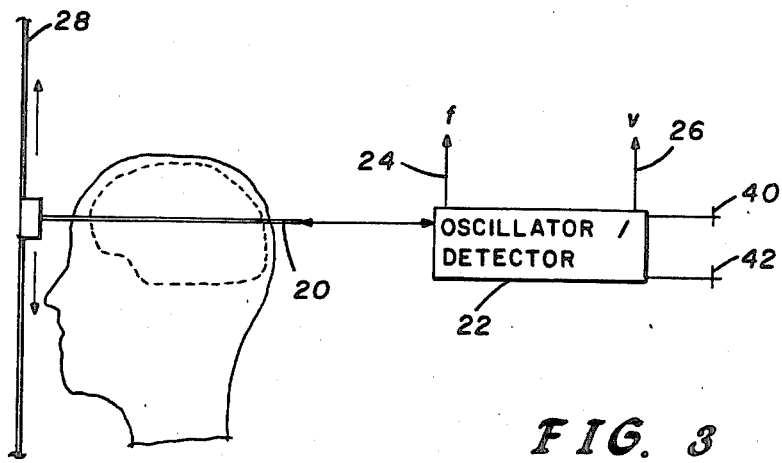
FIG. 3

NON-INVASIVE ELECTROMAGNETIC TECHNIQUE FOR MONITORING PHYSIOLOGICAL CHANGES IN THE BRAIN

STATEMENT OF GOVERNMENTAL INTEREST

The Government has rights in this invention pursuant to Contract No. N00024-85-C-5301, awarded by the Department of the Navy.

BACKGROUND OF THE INVENTION

1. Field of the Invention

The invention relates to a method and apparatus for using an electromagnetic technique to monitor physiological changes in the brain. More particularly, the invention uses an electromagnetic field to non-invasively measure impedance changes at localized points within an animal or human brain. For example, these localized impedance measurements can be used to detect and monitor the advent and growth of edematous tissue, or the process of hydrocephalus.

2. Description of the Prior Art

It is important in diagnosing and treating various life-threatening conditions, such as brain edema and hydrocephalus, to monitor the time-trends of physiological changes in the brain. Brain edema, which is an increase in brain volume caused by grey and/or white brain tissue absorbing edematous fluid, can develop from general hypoxia; from cerebral hemorrhage, thrombosis, or embolus; from trauma (including post-surgical); from a tumor; or from inflammatory diseases of the brain. Brain edema can directly compromise vital functions, distort adjacent structures, or interfere with perfusion. It can produce injury indirectly by increasing intracranial pressure. In short, brain edema is often a life-threatening manifestation of a number of disease processes.

There are several effective therapeutic measures to treat brain edema. These include osmotic agents, corticosteroids, hyperventilation to produce hypocapnia, and surgical decompression. As with all potent therapy, it is important to have a continuous measure of its effect on the manifestation, in this case, the brain edema.

All current techniques for measuring physiological changes in the brain, including the manifestation of brain edema, have shortcomings in providing continuous or time-trend measurements. Intracranial pressure can be monitored continuously, but this is an invasive procedure. Furthermore, intracranial compliance is such that substantial edema must occur before there is any significant elevation in pressure. When the cranium is disrupted surgically or by trauma, or is compliant (as in infants), the pressure rise may be further delayed. These patients are often comatose, and localizing neurological signs are a late manifestation of edema. Impairment of respiration and circulation are grave late signs. Thus, clinical examination is not a sensitive indicator of the extent of edema. X-ray computed tomography (CT) scanning can produce valuable evidence of structural shifts produced by brain edema, and it is a non-invasive procedure. Structural shifts, however, may not correlate well with dysfunction, especially with diffuse edema. Furthermore, frequent repetition is not feasible, particularly with acutely ill patients. NMR proton imaging can reveal changes in brain water, it does not involve ionizing radiation, and it is non-invasive. However, it does not lend itself to frequent repetion in the acutely ill patient. PET scanning can reveal the metabolic disturbances associated with edema and will be invaluable in correlating edema with its metabolic consequences. However, it too is not suited to frequent repetition.

For these reasons it would be a significant advance to have a measurement which (1) gives reliable time-trend information continuously; (2) is non-invasive; (3) does not depend upon the appearance of increased intracranial pressure, and (4) can be performed at the bedside even in the presence of life-support systems.

As will be discussed in detail subsequently in this application, Applicant has related localized impedance changes in the brain with physiological changes in the brain. Applicant was the first to identify that edematous tissue has a significantly different conductivity from healthy white or grey matter.

To non-invasively detect such an impedance change, Applicant has invented a method and apparatus which uses an electromagnetic field for sensing such an impedance change at localized portions of the brain. U.S. Pat. No. 3,735,245 entitled "Method and Apparatus for Measuring Fat Content in Animal Tissue Either in Vivo or in Slaughtered and Prepared Form", invented by Wesley H. Harker, teaches that the fat content in meat can be determined by measuring the impedance difference between fat and meat tissue. The Harker apparatus determines gross impedance change and does not provide adequate spatial resolution for the present use. As will be discussed in detail later, brain impedance measurements must be spatially localized to provide a useful measure of physiological changes. A general measurement of intracranial conductivity would not be revealing, since as in the case of brain edema, the edematous fluid would initially displace CSF fluid and blood from the cranium; and, since these fluids have similar conductivities, a condition of brain edema would be masked.

U.S. Pat. No. 4,240,445 invented by Iskander et al teaches the use of an electromagnetic field responsive to the dielectric impedance of water to detect the presence of water in a patient's lung. The Iskanden et al apparatus generates an electromagnetic wave using a microwave strip line. Impedance changes within the skin depth of the signal will cause a mode change in the propagating wave which is detected by associated apparatus. Therefore, Iskander et al uses a different technique from the present invention and does not detect conductivity variations with the degree of localization required in the present invention. U.S. Pat. No. 3,789,834, invented by Duroux, relates to the measurement of body impedance by using a transmitter and receiver and computing transmitted wave impedance from a propagating electromagnetic field. The Duroux apparatus measures passive impedance along the path of the propagating wave, whereas the present invention measures localized impedance changes in brain matter and fluid by measuring the eddy currents generated in localized portions of the brain matter and fluid. None of the above-cited references contemplate measuring localized impedance changes in the brain to evaluate physiological changes in the brain, such as the occurrence of edematous tissue, and none of the references teach an apparatus capable of such spatially localized impedance measurements.

SUMMARY OF THE INVENTION

Applicant was the first to discover that edematous tissue has a significantly different conductivity (or impedance) from normal white or grey brain matter. Applicant believes that edematous tissue is formed when white or grey matter in the brain becomes diffused or prefused with edematous fluid by an as yet unknown intercellular or extracellular process. As will be described later, the discovery that impedance changes can be used to identify edematous tissue was made using invasive probes. Applicant generally found that the conductivity change between normal and edematous grey tissue, for instance, would change by as much as 0.14 mho/meter, or equivalently by 100% of the normal value.

The present invention detects the increase in conductivity (or decrease in impedance) of brain tissue to locate areas of edematous tissue in the brain. Edematous tissue may occur in localized areas near the surface of the cranium or may occur deeper in the brain. Since edematous tissue swells, blood and CSF fluid in the brain which may have the same conductivity as edema fluid, might be displaced. Therefore, localized spatially discrete changes in impedance must be measured to detect the physiological changes associated with brain edema.

Further, monitoring localized impedance changes in the brain will allow one to measure and diagnose hydrocephalus since an increase in the ventricular volume will result in an increase in conductivity in certain localized areas of the brain. This is because CSF fluid which fills the expanded ventricle has a significantly greater conductivity (1.5–1.75 mho/meter) than white matter (0.10 to 0.15 mho/meter) or grey matter (0.12 to 0.23 mho/meter).

Applicant also realized that such localized impedance changes can be sensed non-invasively using a magnetic field and detecting the changes in mutual inductance between the brain and a sense coil. The apparatus described herein, and also described in part in a copending commonly assigned patent application entitled "Electromagnetic Bone Healing Sensor" (Ser. No. 753,824), generates a spatially discrete oscillating magnetic field which radiates a pre-selected location of the brain. The magnetic field induces eddy currents in brain tissue and fluid in the radiated area. When these eddy currents collapse, they produce a secondary weak magnetic field which is detected by the apparatus. The magnitude of the eddy currents is proportional to the actual impedance of the tissue and fluid where the eddy currents are generated. The magnitude of the eddy currents in turn directly affect the magnitude of the secondary weak magnetic field.

The invented apparatus is capable of detecting small variations in impedance changes and quantitatively measuring such changes. A magnetic drive/sensor means is designed to concentrate the magnetic field in spatially localized areas within the brain. The invention also teaches various techniques for sequentially scanning different pre-selected and localized areas in the brain to generate a composite view of brain impedance. An oscillator detector in combination with the magnetic drive/sensor means is specifically designed to be sensitive to small impedance changes and to reduce polarization effects and background noise which could render such monitoring impossible.

It is hoped that continuous monitoring of a patient at his bedside would enable physicians to treat the first sign of swelling and also to measure any therapy's effectiveness. The invented device may prevent much of the brain damage that results from head injuries, stroke, brain tumors or drug abuse when injured brain tissue swells and presses against the inside of the skull.

BRIEF DESCRIPTION OF THE DRAWINGS

FIG. 1 is a table showing the difference in conductivity between normal and edematous white and grey matter found in a rabbit brain.

FIG. 2 is a graphic representation of the invented non-invasive principal for measuring brain impedance.

FIG. 3 is a block diagrammatic illustration of the present invention showing the use of a drive/sensor loop coil.

FIG. 5a graphically shows the field intensity region for lower frequency excitation; and, FIG. 5b shows the field intensity region for higher excitation frequencies.

FIG. 7a and FIG. 7b illustrate different orientations of the elliptical coil to analyze different areas of the brain.

DETAILED DESCRIPTION OF THE PREFERRED EMBODIMENT

Figure 4:
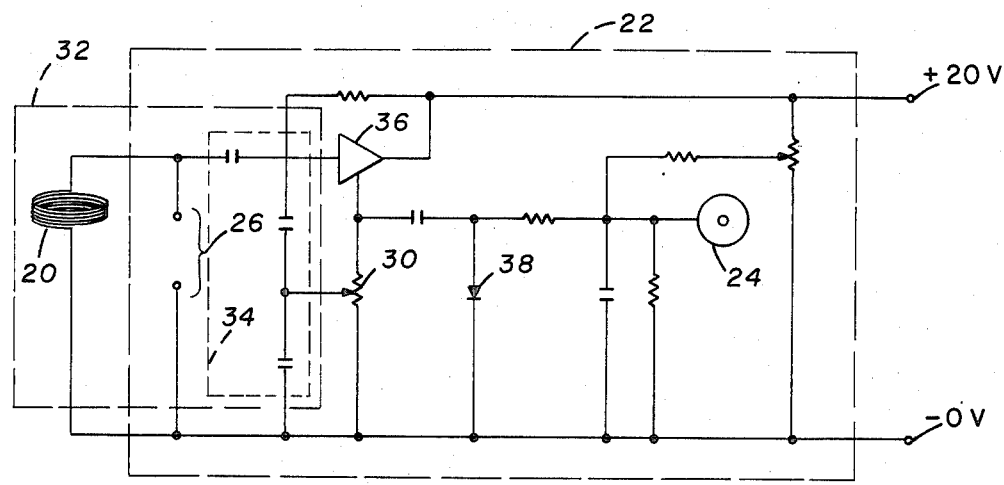
FIG. 4 is a schematic diagram of a typical oscillator/detector circuit used in the present invention.

The present invention provides a method and apparatus for making continuous or time-trend measurements of the migration of CSF and edema fluid within brain tissue and of changes in biological substances in the brain. These biological changes within the brain are monitored by observing changes in local conductivity or impedance within the brain.

Applicant was the first to discover that edematous tissue has a significantly different conductivity (or impedance) from normal white or grey brain matter. Applicant made this discovery using a two-needle probe to contact portions of fresh frozen rabbit brains thawed to room temperature. The rabbit brains contained edematous regions caused by the previous implantation of a rabbit brain tumor. The two-needle probe was connected to an impedance meter for a display of the local impedance value. Impedance measurements were performed with the insertion of a probe needle into normal and edematous white and grey matter as the frozen brains thawed from 4° to 22° C. As shown, in FIG. 1, the edematous grey and edematous white conductivity values were higher than normal tissue. Applicant believes that the higher conductivity in the edematous tissue is because the tissue becomes diffused or prefused with high conductivity edematous fluid. Similar results were obtained at frequencies from one to four megahertz.

FIG. 2 is a schematic representation of a generalized embodiment of the present invention. A drive/sensor coil 10 produces an alternating magnetic field 12. Although the magnetic field intensity lines pass through the brain, the magnetic field intensity lines are more highly concentrated in the plane of the drive/sensor coil 10. The alternating magnetic field (12) generate an electrical field 14 which induces eddy currents in brain tissue and fluid. One such eddy current is graphically represented by element 16 on FIG. 2. The magnitude of the eddy current is proportional to the magnitude of the electric field 14 multiplied by the conductivity of brain tissue and fluid that particular eddy current travels though (i.e., magnitude of eddy current is proportional to $E \times \sigma$ where E is the magnitude of the electric field and $\sigma$ is conductivity). The eddy current alternates in accordance with the alternating magnetic field 12. The alternating eddy current 16 generates a second weaker magnetic field 18. This magnetic field 18 induces a corresponding E field on the sense coil 10 which is detected and processed by the appropriate circuitry.

The sense coil 10 actually detects the secondary magnetic field 18 generated from a multitude of such tiny eddy currents induced in the brain tissue and fluid excited by the primary magnetic field 12. Since we are interested in localized impedance measurements, spatial and temporal techniques are used to either reduce the area of brain excitation by the primary magnetic field 12 or temporally separating the reception of secondary magnetic field 18 from a selected area of the brain. In the generalized embodiment shown in FIG. 2, the drive/sensor loop coil 10 produces some degree of localization by intensifying the magnetic field in the plane of the coil 10.

FIG. 3 is a schematic representation of a non-invasive apparatus to measure localized brain impedance as taught by the present invention. The drive/sensor coil is a thin or narrow magnetic field coil winding 20. Oscillator/Detector 22 provides an alternating electric current in coil 20 which produces an alternating magnetic field. As brain tissue and fluid are brought within the proximity of coil 20, the mutual inductance of the coil changes the frequency of oscillation of the oscillator/detector 22. The magnitude of the frequency change is proportional to the value of the electrical conductivity located within the drive/sensor coil 20. In summary, the magnetic field produced by the drive/sensor coil 20 creates an electric field. The electric field creates induced eddy currents within the brain tissue and fluid. These induced eddy currents re-radiate a secondary magnetic field, which is detected by the drive/sensor coil 20 and in effect changes its mutual inductance. The change in mutual inductance of the coil changes the oscillator frequency of the oscillator/detector 22 to correspondingly change.

Returning to FIG. 3, a patient's head would be placed through detector coil 20 which non-invasively ascertains the electrical conductivity in a horizontal section of the brain. Oscillator/detector 22 is connected to the coil 20 and generates an oscillating magnetic signal in the coil. The change in mutual inductance of the coil is picked up by oscillator/detector 22 and results in a change in output 24 indicating a frequency change and in output 26 indicating a voltage change. The magnitude of electrical conductivity (or impedance) of a particular horizontal section of the brain is thus detected.

In this embodiment the drive/sensor coil 20 would operably slide on a track 28, so that a series of horizontal sections of the head can be measured.

FIG. 4 is a schematic drawing of one possible circuit configuration for oscillator/detector 22. Electronically, the circuit represents a marginally stable Colpitts oscillator whose frequency of oscillation is determined by the tank circuit. Although a Hartley-type oscillator, or similar, would work equally well. The potentiometer tap 30 helps to find the proper circuit resistance external to the tank circuit 32 resistance that is needed for stable oscillation. The tank circuit 32 includes coil 20 and capacitors 34. The amplifier 36 with negative feedback provides stable voltage gain. A DC output 24 is extracted from the demodulator diode 38 which reflects the change in oscillator amplitude. The frequency is measured directly off coil 20 at output 26. When a patient's head is placed through coil 20, eddy currents are induced by the time changing magnetic field generated by drive/sensor coil 20. The eddy currents in turn produce a secondary, though slight, magnetic field whose associated field is coupled back to the drive/sensor coil 20. This produces a change in the coil impedance which changes the resonant amplitude, measured at output 24, and the resonant frequency, measured at output 26, of tank circuit 32. The coil inductances are in the millihenry (mH) range so that resonant frequencies in the hundreds of kHz to several MHz are obtained. In this frequency range, the impedance changes are dominated by conductivity properties and not polarization effects caused by the relative permittivity of the media.

Figure 5A:
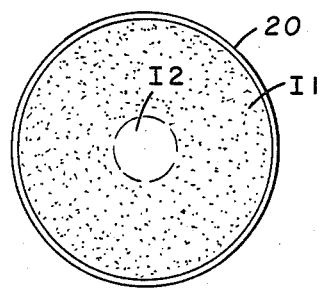
FIGS. 5a and b illustrate spatial localization within a drive/sensor loop coil by varying the frequency of the exciting electrical signal.
Figure 5B:
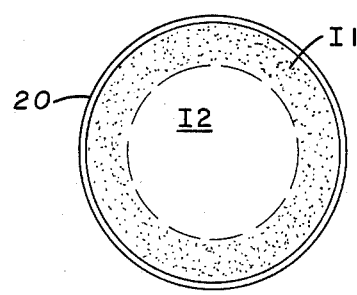

The loop drive/sensor loop coil 20, shown in FIG. 3, tends to generate a magnetic field which is concentrated in the plane of the drive/sensor coil and which extends above and below the horizontal plane of the drive/sensor coil. Varying the frequency and the waveform of the magnetic field can produce further spatial discrimination. As shown in FIG. 5, which illustrates the exciting magnetic field strength in the plane of the drive/sensor coil, a change in the frequency of the oscillating magnetic field changes spatial discrimination in the plane of the drive/sensor coil. Higher frequency excitation will increase the magnetic field intensity near the surface of the cranium and a lower frequency will increase the depth of penetration toward the center of the brain. By selectively adjusting the frequency and waveform of the generated magnetic field, using controls 40 and 42 respectively (see FIG. 3) the spatial discrimination provided by the drive/sensor coil can be varied. By observing the outputs from the oscillator detector (24/26) as the frequency and waveform of the exciting magnetic field are change (via controls 40 and 42) an impedance map can be generated and small impedance changes in the brain can be localized.

Figure 6:
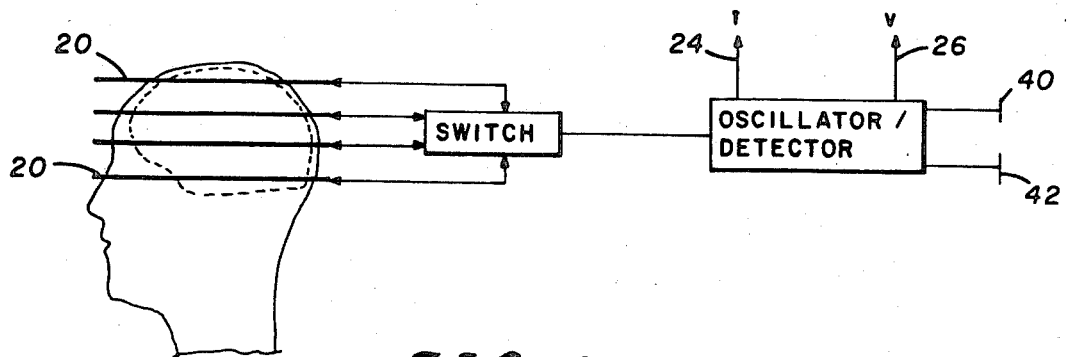
FIG. 6 is a block diagrammatic illustration of the present invention using a plurality of drive/sensor loop coils to map out local areas of impedance.

The planar drive/sensor loop technique may be implemented to examine selective slices through the head. The apparatus for selectively examining such slices can be a means 28 shown in FIG. 3 for accurately positioning the drive/sensor loop 20 at a plurality of positions. The outputs (24, 26) resulting from each of the overlapping slices, can be analyzed and the location of higher conductivity areas in the brain tissue can be identified. Alternatively, as shown in FIG. 6, a plurality of drive/sensor coils 20 can be used, with each coil interrogated sequentially. Again, the outputs (24, 26) from each indicates the overall impedance value for that horizontal slice. By looking at a plurality of such slices one can map out localized impedance in the brain. Alternatively, several loop coils can be energized at the same time with opposing magnetic fields to better focus the area of excitation.

It is to be understood that such drive/sensor coils may be vertically or horizontally oriented; or, the arrangement may be such that both horizontal and vertical orientations are used to increase spatial resolution. The individual impedance measurements made from each of the plurality of planar loops can be resolved into an overall image of the impedance footprint by known signal processing methods.

Figure 7A:
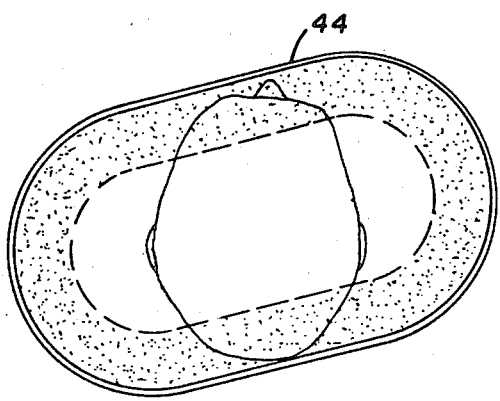
FIGS. 7a and b illustrate the use of an elliptical drive/sensor coil.
Figure 7B:
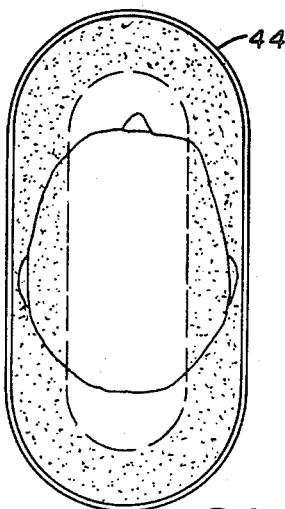

Alternatively, the planar loop can have an elliptical cross section (e.g., ellipse) to allow its rotation to selectively examine sections around the head. FIGS. 7a and b illustrate the design of the elliptical drive/sensor loop 44. Since the region associated with the smaller axis of the elliptical coil has increased sensitivity to impedance change, as the elliptical coil is rotated and the outputs (24,26) observed with changing orientation of the elliptical coil, a plot can be generated which will assist in localizing high impedance regions within the brain. It is envisioned that a plurality of such elliptical loops may be used sequentially to map brain impedance.

Figure 8:
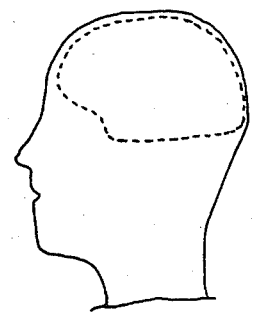
FIG. 8 is a schematic diagram showing a solenoid type drive/sensor coil.
Figure 9:
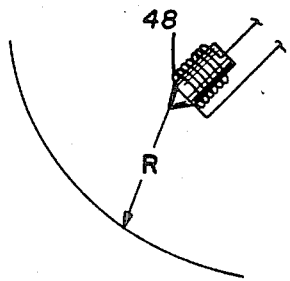
FIG. 9 is a graphic illustration showing radius R of higher field intensity for a solenoid coil.

FIG. 8 is a block diagram of the apparatus showing the use of a solenoid-type coil 48 for the drive/sensor coil. The solenoid-type coil 48 operates similarly to the loop coil (see FIG. 3), except that the solenoid coil shows a maximum response to the samples within a localized volume at the tip of the solenoid coil approximately equal to the diameter of the solenoid coil while the planar loop shows a response to the higher conductivity portions of the sample in almost any position in the coil plane. The solenoid-type coil may have an air core or may use a metal core to further concentrate the magnetic field and localize the area of observation (i.e., increase the spatial resolution). The solenoid-type coil has a more localized, but limited range and would be more useful to detect physiological changes near the surface of the brain. This makes this embodiment ideal to localize and monitor edematous tissue caused by surface trauma or surface tumors. As with the loop coil, the spatial resolution of the solenoid-type coil can be adjusted by varying the frequency of the exciting magnetic field (via control 40) or varying the waveform characteristics of the magnetic field (via control 42). The radius R of higher field intensity is shown in FIG. 9. As the frequency of the magnetic field increases, the radius R shown in FIG. 9, which represents the region of high magnetic field intensity decreases.

Figure 10:
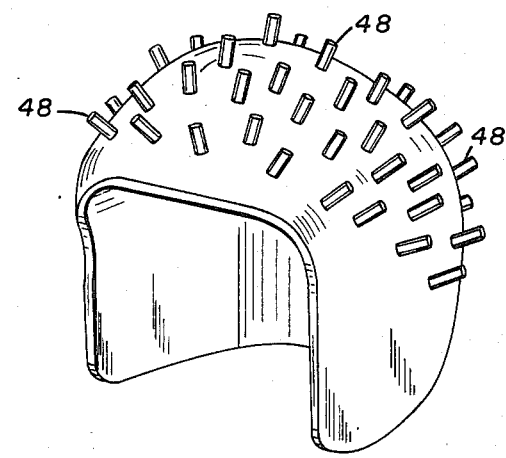
FIG. 10 illustrates a bonnet type embodiment to be worn on the patient's head having a plurality of solenoid type drive/sensor coils.

FIG. 10 shows a set of solenoid-type coils 48 placed around the head in a bonnet. Each coil is sequentially energized by the oscillator/detector 22 and determines the impedance in the localized area of the brain near the cranium surface. The various impedance measurements thus obtained can be mapped to show overall brain impedance and to localize areas of edematous tissue. It is within the contemplation of this invention to use solenoid-type coils in cooperation with planar coils to obtain a more complete picture of the brain impedance.

The embodiments discussed thus far were directed to a monostatic system that uses the same coil as both the transmitter coil and receiver coil. This invention also contemplates the use of a bistatic system in which two coils are used. In the bistatic apparatus, shown in FIG. 11, a first transmitter coil 50 is located on one side of the brain and a second receiver coil 52 is located on the opposite side of the brain. The two coils are connected to an oscillator/detector 54. The transmitter coil 50 excites eddy currents in the brain fluid and matter. The secondary weak magnetic field generated by these eddy currents are detected by receiver coil 52. The bistatic apparatus may use a continuous excitation wave or it may use pulsed excitation.

Figure 12:
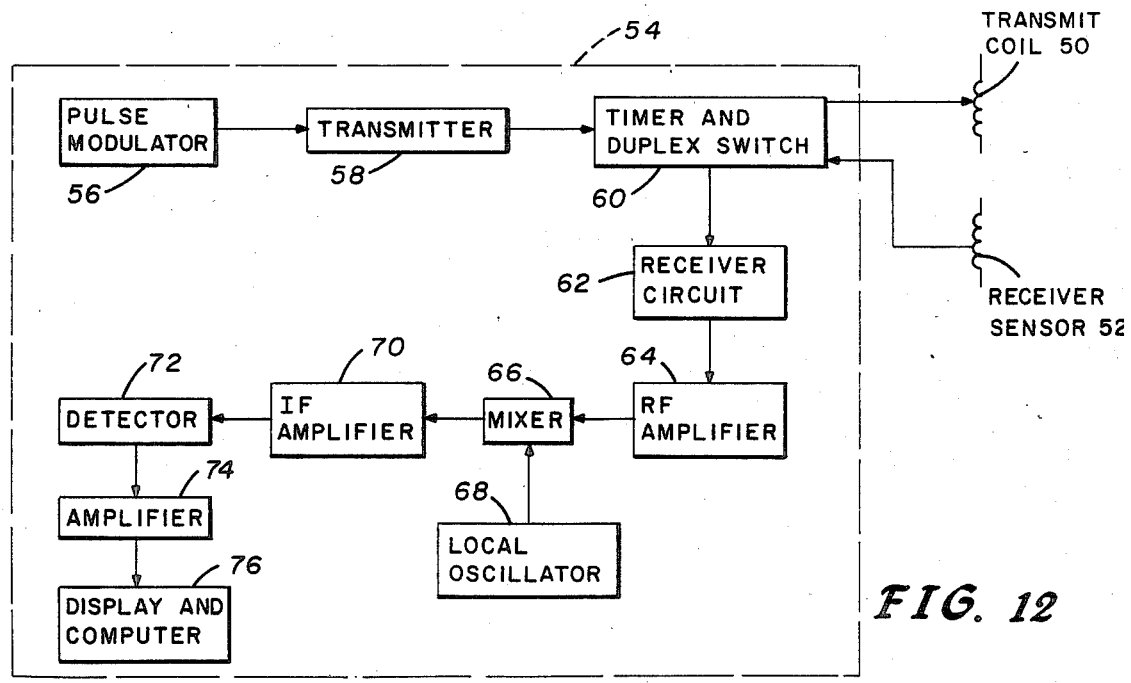
FIG. 12 is a schematic block diagram of a typical circuit used for either monostatic or bistatic pulsed excitation.

FIG. 12 is a block diagram of the oscillator/detector 54 for use with pulsed excitation. The basic idea behind the pulsed measurement relies on the principal of dispersion. The transmitter would transmit a pulse, not a continuous wave, of magnetic energy. As the pulse travels through the brain, the pulse shape changes because of the dispersive characteristic of brain matter. In effect, dispersion causes different wavelength components of the original pulse to travel at different speeds. Therefore, if different wave components travel at different speeds at any range away from the initial pulse transmission site, the collection of wavelengths are added to give a composite pulse with a different shape. This dispersive characteristic can be designed into a compressed pulse technique whereby the composite pulse can be designed to have a maximum amplitude at a particular range, that is, relying on the dispersive properties of the medium to change the waveform of the transmitted pulse so that it reaches a peak at a designated range. This situation is analogous to a handicapped horse race event where the horses are given a staggered start so that they all end up at the finish line at the same time. The advantage of the compressed pulse technique is that it allows us to concentrate pulse energy at designated ranges, thereby giving us the ability to interrogate designated regions of the brain; that is, we do not get a large sensor response at places other than the designated range. The receiver sensor can receive an output proportional to the change at the designated range by a technique called "range gating", whereby the receiver would only look for a signal at designated times.

Figure 11:
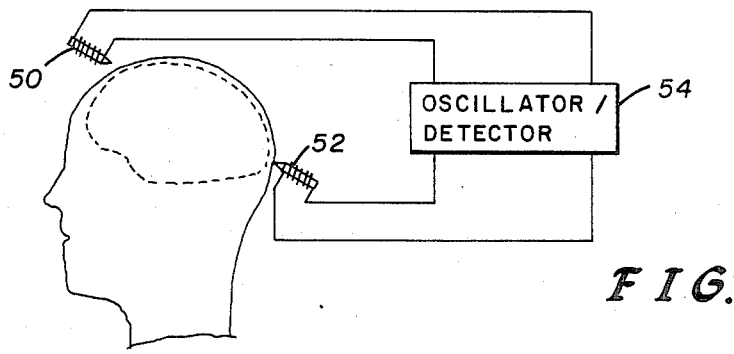
FIG. 11 is a block diagrammatic illustration of a bistatic technique as taught by the present invention.

FIG. 12 is a block diagram of such a pulsed circuit configuration. A pulse modulator 56 creates the desired waveform and generates a repetitive train of pulses. The transmitter 58 amplifies the pulses for suitable transmission by the transmitter coil 50. The timer and duplex switch 60 decides when to energize the transmitter sensor 50. The received signal is sensed by the receiver sensor 52 and sent to the timer and duplex switch 60, which decides when to send the received signal to the receiver circuit 62. In the monostatic configuration, sensor 50 and 52 may be the same coil. The receiver circuit 62 may be the circuit shown in FIG. 4. The RF signal from the receiver circuit 62 is amplified by the RF amplifier 64 and then sent to the mixer 66. The mixer 66 and local oscillator 68 convert the RF signal to an IF signal which is amplified by the IF amplifier 70. The IF amplifier 70 may be a matched filter designed to maximize the signal power from knowledge of the desired signal morphology. The detector 72 extracts the signal from the pulse modulation. The unmodulated signal is then amplified 74, displayed, and analyzed by computer 76. In this manner the impedance in different areas along the axis between the transmitter coil 50 and receiver coil 52 (see FIG. 12) can be measured. It would also be envisioned to have a plurality of transmitter coil/sensor coil pairs (as shown in FIG. 11) and thereby map out three-dimensional images of brain impedance.

Obviously many modifications and variations of the present invention are possible in light of the above teachings. It is therefore to be understood that within the scope of the appended claims, the invention maybe practiced otherwise than is specifically described.

What is claimed is:

1. A method for locating edematous tissue within the white or grey matter of an animal or human brain, comprising:

noninvasively detecting the impedance due to brain tissue and other biological matter at a plurality of localized portions within the brain, wherein said detecting step for each of said plurality of localized portions comprises the steps of:
   a. producing an oscillating magnetic field that is spatially concentrated in a localized portion of a brain using a coil means, whereby eddy currents induce a secondary magnetic emission which alters the mutual inductance of said coil means in accordance with the impedance of brain tissue and other biological matter in said portion, and
   b. measuring a change in the mutual inductance of said coil means, wherein an increase in mutual inductance indicates an increase in impedance and a decrease in mutual inductance indicates a decrease in impedance; and, comparing the impedance detected at each portion of the brain to determine the location of higher impedance regions within the white or grey matter of the brain that indicate the location of edematous tissue.

2. The method of claim 1 wherein said producing step involves the step of generating a spatially concentrated magnetic field in a horizontal section of the brain using a loop coil adapted to encompass a patient's cranium.

3. The method of claim 1 wherein said producing step involves the step of generating a concentrated magnetic field for each portion using a solenoid coil positioned proximal to the surface of a patient's cranium.

4. The method of claim 1, wherein said producing step involves the step of varying the spatial concentration of said magnetic field by varying the frequency of said magnetic field.

5. The method of claim 1, wherein said producing step involves the step of varying the spatial concentration of said magnetic field by varying the waveform of said magnetic field.

6. The method of claim 4 or 5, wherein said measuring step involves detecting changes in mutual inductance as the spatial concentration of said magnetic field is varied.

7. The method of claim 1, further comprising the step of:

mapping impedance contours of at least a section of the brain to located edematous tissue using the magnitude of mutual inductance detected for a particular localized portion of the brain, wherein localized portions having a higher concentration of edematous tissue will produce a higher mutual inductance.

* * * * *